United States Patent [19]
Joulak et al.

[11] Patent Number: 5,554,299
[45] Date of Patent: Sep. 10, 1996

[54] TREATMENT/REMOVAL OF BYPRODUCT AQUEOUS EFFLUENTS COMPRISING HYDROXYNITROAROMATIC COMPOUNDS

[75] Inventors: Faouzi Joulak, Chesnay; Louis Le Bris, Lyons; Philippe Marion, Villeurbanne, all of France

[73] Assignee: Rhone-Poulenc Chimie, Courbevoie Cedex, France

[21] Appl. No.: 367,873

[22] Filed: Jan. 3, 1995

[30] Foreign Application Priority Data

Dec. 31, 1993 [FR] France ..................................... 93 15988

[51] Int. Cl.$^6$ .................... C02F 1/52; C02F 1/66
[52] U.S. Cl. .................. 210/712; 210/724; 210/909; 568/932; 568/934
[58] Field of Search .................................... 210/712, 724, 210/749, 909; 568/932, 934

[56] References Cited

U.S. PATENT DOCUMENTS

| | | | |
|---|---|---|---|
| 3,221,064 | 11/1965 | Brogden et al. | 568/934 |
| 4,361,712 | 11/1982 | Herman et al. | 568/932 |
| 4,482,769 | 11/1984 | Toseland et al. | 568/934 |
| 4,597,875 | 7/1986 | Carr et al. | |
| 4,604,214 | 8/1986 | Carr et al. | |

*Primary Examiner*—Peter A. Hruskoci
*Assistant Examiner*—Theodore M. Green
*Attorney, Agent, or Firm*—Burns, Doane, Swecker & Mathis, L.L.P.

[57] ABSTRACT

Objectionable byproduct aqueous effluents containing contaminating amounts of hydroxynitroaromatic compounds, in particular those aqueous effluents produced during the synthesis of nitroaromatic compounds, e.g., dinitrotoluenes, via reaction of an aromatic compound with nitric acid in the presence of sulfuric acid, are efficiently, facilely and economically treated/removed by (a) intimately contacting a mixture of at least one nitroaromatic compound and at least one hydroxynitroaromatic compound with an aqueous wash medium containing a neutralizing agent, (b) separating the resulting admixture into an organic phase and an aqueous phase, (c) recycling a fraction of the separated aqueous phase to the aqueous wash medium to thus constitute a portion thereof, and (d) periodically draining a fraction of the wash medium, whether to destruction thereof or to waste.

13 Claims, No Drawings

TREATMENT/REMOVAL OF BYPRODUCT AQUEOUS EFFLUENTS COMPRISING HYDROXYNITROAROMATIC COMPOUNDS

BACKGROUND OF THE INVENTION

1. Field of the Invention

The present invention relates to the elimination of byproduct aqueous effluents comprising hydroxynitroaromatic type compounds, and, more especially, to the removal of byproduct aqueous effluents which result during the preparation and purification of nitroaromatic compounds via reaction of aromatic compounds with nitric acid in the presence of sulfuric acid.

2. Description of the Prior Art

It is known to this art that, following nitration of aromatic compounds, the reaction medium is treated to separate the desired nitroaromatic compounds thus produced from the mineral acids employed as reactants and as catalyst, then from the byproducts formed.

This operation normally includes a number of successive wash steps, each followed by a decantation/separation cycle for the organic and aqueous phases. Thus, the reaction medium is first contacted with water to recover the nitric and sulfuric acids. One or more washes are then carried out using water containing a neutralizing agent to eliminate the byproducts.

By the term "byproducts" are intended hydroxyaromatic compounds containing one, two or three nitro groups (such as nitrophenols and nitrocresols). These compounds are the most objectionable, as they are known to poison the catalysts used in the final hydrogenation reaction to which the nitroaromatic compounds may be subjected. This reaction reduces the nitro groups to amine groups and the resulting amines can then be used as reactants for the production of compounds such as isocyanates.

The term "byproducts" also comprehends aromatic carboxylic acid compounds containing one, two or three nitro groups and carboxylic acids containing one to six carbon atoms, such as formic, acetic or oxalic acid.

These byproducts, a representative number of which having been indicated above, are designated either as byproducts or as hydroxynitroaromatic compounds in the description that follows.

Treatment and/or elimination of the aqueous phase recovered after the various washing steps, corresponding to separation of the nitroaromatic compounds from the byproducts formed, presents a serious disadvantage as the quantity of these byproducts is considered to be too great. Consequently, the effluents cannot be discharged without prior treatment.

One possible solution to this problem is to collect the effluents and incinerate them, optionally following concentration thereof. However, this technique is not economically viable because the cost of both concentrating the effluents and then incinerating them is too high. In addition, this technique does not eliminate the problem of discharging the inorganic compounds used, particularly for the neutralization step.

Another possible solution is to extract the byproducts, principally the hydroxynitroaromatic compounds, by means of a suitable solvent, then concentrating and incinerating the extracted species. However, this operation is also of no economic interest because of the multiplicity of steps (extraction, concentration) and the requirement for additional reagents.

Chemical or biochemical treatment of aqueous effluents prior to their discharge to destroy byproducts present in the aqueous phase is also known to this art. These methods, however, can also be very costly and entail an extra step in the sequence. In addition, a very large amount of water is discharged, and even if the hydroxynitroaromatic compounds have been removed, the water nevertheless contains a significant fraction of neutralizing agent which is lost and which should be destroyed before discharging the effluent to waste.

It will thus be seen that no efficient and economically advantageous treatment currently exists to combat the problem of waste water emanating from an aromatic compound nitration process.

SUMMARY OF THE INVENTION

Accordingly, a major object of the present invention is the provision of an improved process for the treatment/removal of contaminated wastewater emanating from the synthesis of nitroaromatic compounds, and which combines efficiency, simplicity of operation and minimal cost.

Briefly, the present invention features the treatment of aqueous effluents containing hydroxynitroaromatic compounds, in which a mixture of nitroaromatic compounds and hydroxynitroaromatic compounds is intimately contacted with a washing medium containing water and a neutralizing agent, then separating the resulting organic and aqueous phases, and further wherein (i) said washing medium is partially constituted by the separated aqueous phase which is recycled, and (ii) a fraction of the washing medium is periodically drained for destruction.

DETAILED DESCRIPTION OF BEST MODE AND PREFERRED EMBODIMENTS OF THE INVENTION

More particularly according to the present invention, the subject process presents a number of advantages. Aqueous effluent does not have to be discharged and this is achieved without the requirement for added process steps or for additional reagents, such as solvents or agents which destroy or consume the byproducts. In addition, recycling the wash water from the reaction medium considerably reduces neutralizing agent losses and makes destruction (for example by incineration) or final discharge of effluent very attractive economically.

In one embodiment of the invention, the pH of the aqueous phase ranges from 5 to 8.

Preferably, the pH of the aqueous phase ranges from 6 to 8.

It should be noted that operating under conditions in which the pH of the aqueous phase exceeds the value indicated is possible, even though this is of no particular advantage.

In a first embodiment of the process of the invention, the mixture to be treated may also contain a cosolvent for the nitroaromatic compounds produced.

Exemplary such cosolvents include $C_6$-$C_{10}$ aromatic compounds, which may be substituted by hydrocarbon radicals and/or halogenated. Specific examples thereof are toluene, cumene and chlorobenzene.

In a second embodiment of the invention, the mixture to be treated does not contain any cosolvent.

The operation can be carried out in one or more steps, with stirring.

As is conventional, the mixture and washing medium are contacted at a temperature ranging from 20° C. to 90° C. In the particular event where the mixture does not contain a cosolvent, the temperature preferably ranges from 60° C. to 80° C.

This operation is typically carried out at a pressure ranging from 0.5 to 10 bar. Advantageously, it is close to atmospheric pressure.

The contact time in each step is advantageously on the order of several minutes to 2 hours.

Following contacting of the mixture to be treated with the washing medium, the resulting admixture is decanted and the organic phase containing the purified nitroaromatic compounds is separated from the aqueous phase containing the byproducts in the form of salts thereof.

The process of the invention may include one or more washes.

The essential characteristic of the invention is that the washing medium is partially constituted by the recovered aqueous phase which is recycled to the washing process. In addition, a fraction of said washing medium is periodically drained before destruction (incineration, discharge).

In a preferred embodiment of the invention, the washing medium is recycled such that the concentration of byproducts is increased by a factor of 10 with reference to the amount present in the aqueous phase from the first wash. Recycling is preferably carried out such that the concentration of byproducts is increased by a factor of at least 20, up to a factor of 30.

It should be appreciated that the process can be operated under conditions where the concentration is outside the values indicated above. However, if the concentration is increased by a factor of less than 10, the advantages presented by recycling are less marked. Similarly, a concentration of more than 30 times the original concentration risks polluting the organic phase by transfer of byproducts to the organic phase, thus presenting difficulties during the hydrogenation reaction.

The drained fraction advantageously represents 3% to 10% by weight of the total amount of washing medium.

Since the process of the invention is preferably carried out continuously, draining a fraction of the washing medium necessitates adding an amount of washing medium corresponding to the quantity drained. It will be appreciated that this constitutes an additional advantage of the subject process. Indeed, contrary to conventional processes which do not include a recycling step, the amount of washing medium introduced into the sequence is considerably less than that normally used (3% to 10%).

This addition can be carried out at any situs in the process zone where the mixture of nitroaromatic compounds and byproducts is washed.

The washing apparatus is conventional and one skilled in this art could use one or more storage reservoirs for the washing medium, positioned between two washing tanks.

Following the washing step(s), the organic phase, which has been separated from the aqueous phase, can if necessary be washed with water to recover all traces of neutralizing agent.

The resulting effluent, which may contain trace amounts of neutralizing agent, can be discharged, if necessary following a purification treatment.

This washing water, however, is advantageously recycled to the process of the invention. In particular, the stream can be reintroduced to the first washing step which eliminates the mineral acids from the nitration reaction products.

The process of the invention is normally carried out with stirring at a temperature ranging from 20° C. to 90° C., for a period of time of several minutes to 2 hours.

The resulting mixture is then decanted and the organic phase, containing the nitroaromatic compounds, is separated from the aqueous phase.

Said purified nitroaromatic compounds can then be used for the preparation of aromatic diamines.

The nitroaromatic compounds, if necessary after drying by any known means, are then reacted with pure or diluted hydrogen in the presence of a conventional hydrogenation catalyst, for example Raney nickel or a platinum based catalyst.

The hydrogenation reaction temperature generally ranges from 80° C. to 200° C. and the pressure during the reaction advantageously ranges from 1 to 150 bar.

In order to further illustrate the present invention and the advantages thereof, the following specific example is given, it being understood that same is intended only as illustrative and in nowise limitative.

EXAMPLE

A dilute aqueous ammonia solution and a mixture of dinitrotoluenes containing trinitrocresols were introduced, in parallel, into a stirred continuous reactor communicating with a decanter positioned downstream thereof.

The temperature was 70° C. and the residence time in the washing and decanting zone was one hour.

The dinitrotoluenes had already been washed in a first washing step to eliminate the mineral acids present during the nitration reaction.

The amount of organic acid species in this mixture, principally containing nitrocresols, was 1,300 ppm.

The dinitrotoluene and dilute ammonia flow rates were 500 g/h and 150 g/h, respectively.

A minimum of 90% of the aqueous phase from the decanter was recycled and reintroduced into the reactor at a recycle flow rate of 135 g/h.

Once recycling had commenced, the ammonia flow rate was reduced to 10% of the total flow rate, i.e., 15 g/h. This addition was such that the pH of the aqueous phase was maintained at a constant value within the range 7–8.

The added neutralizing agent was continuously drained for incineration.

The concentration of byproducts (nitrocresols, nitrophenols, nitrobenzoic acids) and that of the inorganic species (ammonium ions from the neutralizing agent, nitrates, residual sulfates not extracted during the first washing step) was increased via this technique.

A 1% concentration of byproducts was attained in this instance.

The nitrotoluenes obtained were washed with water at 70° C. in a second reactor, also communicating with a downstream decanter, and were then transferred to another reactor for hydrogenation.

A hydrogenation test was carried out on the resulting nitrotoluenes to provide quality control.

This test entailed introducing the nitrotoluenes into a stirred reactor containing isopropanol and Raney nickel at a temperature of 130° C., under a hydrogen atmosphere and at a total pressure of 35 bar.

The degree of hydrogenation was obtained by measuring the pressure of hydrogen which had to be introduced into the reactor to maintain the total pressure at 35 bar.

This test evidenced that the degree or extent of hydrogenation of the nitrotoluenes obtained employing the process of the invention was identical to that of the nitrotoluenes obtained employing the same washing steps, but without recycling.

Thus, the process of this invention did not adversely affect the quality of the nitrotoluenes produced.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the treatment/removal of byproduct aqueous effluent containing contaminating amounts of hydroxynitroaromatic compounds, comprising (a) intimately contacting a mixture of at least one nitroaromatic compound and at least one hydroxynitroaromatic compound with an aqueous wash medium which comprises a neutralizing agent,
   (b) separating the resulting admixture into an organic phase and an aqueous phase, (c) recycling a fraction of said separated aqueous phase to said aqueous wash medium,
   (d) periodically draining from 3% to 10% of the total amount of said aqueous wash medium, and
   (e) adding a replenishing amount of aqueous wash medium corresponding to the drained fraction thereof.

2. The process as defined by claim 1, said neutralizing agent comprising a reactant that converts said at least one hydroxynitroaromatic compound into a water soluble salt thereof.

3. The process as defined by claim 2, said neutralizing agent comprising an alkali and/or alkaline earth metal hydroxide, carbonate or bicarbonate, or ammonia.

4. The process as defined by claim 1, wherein the concentration of said neutralizing agent in said aqueous wash medium ranges from 0.1% to 50% by weight.

5. The process as defined by claim 4, said concentration ranging from 2% to 20% by weight.

6. The process as defined by claim 1, wherein the pH during intimate contacting of said nitroaromatic/hydroxynitroaromatic compound mixture with said aqueous wash medium ranges from 5 to 8.

7. The process as defined by claim 6, said pH ranging from 6 to 8.

8. The process as defined by claim 1, said intimate contacting being at a temperature ranging from 20° C. to 90° C.

9. The process as defined by claim 8, said temperature ranging from 60° C. to 80° C.

10. The process as defined by claim 1, said at least one nitroaromatic compound comprising a nitro- or polynitrotoluene.

11. The process as defined by claim 1, said at least one hydroxynitroaromatic compound comprising a nitro- or polynitrophenol, a nitro- or polynitrocresol, a nitro- or polynitroaromatic carboxylic acid, or mixture thereof.

12. The process as defined by claim 1, further comprising recovering said at least one nitroaromatic compound from said separated organic phase.

13. The process as defined by claim 1, comprising a plurality of contacting/separating sequences.

* * * * *